United States Patent
Simon et al.

(10) Patent No.: US 9,161,892 B2
(45) Date of Patent: Oct. 20, 2015

(54) MOUTHWASH

(75) Inventors: Eric Simon, Somerset, NJ (US); Linh Fruge, Hillsborough, NJ (US); Karsten Kohrs, Berkley Heights, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/420,457

(22) PCT Filed: Aug. 10, 2012

(86) PCT No.: PCT/US2012/050269
§ 371 (c)(1),
(2), (4) Date: Feb. 9, 2015

(87) PCT Pub. No.: WO2014/025355
PCT Pub. Date: Feb. 13, 2014

(65) Prior Publication Data
US 2015/0196469 A1    Jul. 16, 2015

(51) Int. Cl.
*A61K 8/22* (2006.01)
*A61K 8/81* (2006.01)
*A61K 8/49* (2006.01)
*A61K 8/60* (2006.01)
*A61K 8/362* (2006.01)
*A61K 8/24* (2006.01)
*A61K 8/365* (2006.01)
*A61Q 11/00* (2006.01)

(52) U.S. Cl.
CPC ... *A61K 8/22* (2013.01); *A61K 8/24* (2013.01); *A61K 8/362* (2013.01); *A61K 8/365* (2013.01); *A61K 8/49* (2013.01); *A61K 8/60* (2013.01); *A61K 8/8129* (2013.01); *A61Q 11/00* (2013.01)

(58) Field of Classification Search
USPC ................................... 424/53, 616
See application file for complete search history.

(56) References Cited

U.S. PATENT DOCUMENTS

| | | | |
|---|---|---|---|
| 6,447,757 B1 | 9/2002 | Orlowski et al. | |
| 7,354,604 B2 * | 4/2008 | Ramirez et al. | 424/616 |
| 7,803,353 B2 | 9/2010 | Lee et al. | |
| 2007/0116831 A1 | 5/2007 | Prakash et al. | |
| 2008/0025926 A1 * | 1/2008 | Kavouklis et al. | 424/53 |
| 2008/0318834 A1 * | 12/2008 | Cadee et al. | 514/2 |

FOREIGN PATENT DOCUMENTS

| | | |
|---|---|---|
| JP | 2004-210721 | 7/2004 |
| JP | 2008-201732 | 9/2008 |
| WO | WO 00/62749 | 10/2000 |

OTHER PUBLICATIONS

International Search Report and Written Opinion for International Application No. PCT/US2012/050269 mailed on Jun. 13, 2013.

* cited by examiner

*Primary Examiner* — Walter Webb

(57) ABSTRACT

The invention provides mouthwash formulations having improved taste, coupled with good whitening efficacy, which comprise a whitening agent such as hydrogen peroxide together with a combination of a first acid such as citric acid and a second acid such as phosphoric acid. In further embodiments, the mouthwashes may comprise a sucralose and saccharin combination, an acidic polymer, one or more anticalculus agents, e.g., alkali pyrophosphate salts, copolymers of maleic anhydride and methyl vinyl ether and other ingredients.

13 Claims, No Drawings

MOUTHWASH

BACKGROUND

Whitening agents such as hydrogen peroxide ($H_2O_2$) provides whitening benefit in mouthwash, but peroxide-based mouth rinses are often associated with a bitter off-taste. Saccharin, commonly used as a sweetener in mouthwashes, may have a strong bitter after taste that is particularly noticeable in formulations comprising $H_2O_2$. Moreover, $H_2O_2$ is especially prone to degradation at high pH, and to minimize the peroxide degradation, a mouthwash formula with $H_2O_2$ is generally formulated below pH 5.5, the pH often being adjusted by the addition of an acid, which may give an unpleasantly sour taste.

There is a need for a mouthwash that provides whitening benefits, but also is palatable and has a pleasant taste.

SUMMARY

The present invention provides mouthwash formulations having improved taste, coupled with good whitening efficacy, which comprise an effective amount of a whitening agent such as hydrogen peroxide together with a combination of a first acid, such as citric acid and a second acid, such as phosphoric acid. For example, the phosphoric acid lowers the pH of the mouthwash formulation, and citric acid is used to provide a strong buffer capacity at pH 4-5.5. Phosphoric acid with $pK_a$ of 2.1, 7.2 and 12.4, is not a good buffer for the desired pH, while citric acid with $pK_a$ of 4.74 provides a better buffer for the desired pH. Citric acid has stronger acidic note relative to phosphoric acid, and the combination of two acids provides a more acceptable acidic taste in the final formulation compared to either of the two acids separately. In a further embodiment, the invention provides a use of sucralose and saccharin combination to provide a sweet taste with minimized bitter note, compared to a formulation with saccharin alone, which proves to have a strong bitter aftertaste. In further embodiments, the mouthwash may comprise an acidic polymer, for example a polymer selected from polycarboxylate polymers and polyvinyl methyl ether/maleic anhydride (PVME/MA) copolymers, which is found to further improve the palatability as well as the viscosity of the mouthwash and to enhance the stability of the peroxide, the mouthwash further comprises one or more anticalculus agents, e.g., alkali pyrophosphate salts, and the mouthwash may contain flavoring/cooling agents, e.g. comprising a combination of menthol and methyl salicylate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

In one embodiment, the invention provides a mouthwash comprising a whitening agent in an amount effective to whiten the teeth, together with a buffer system comprising a first acid with a $pK_a$ of 4-5.

One aspect of this embodiment is that the whitening composition comprises as a whitening agent at least one peroxy compound, optionally together with one or more additional whitening agents such as chlorine dioxide, chlorites and hypochlorites (e.g., chlorites and hypochlorites of alkali and alkaline earth metals such as lithium, potassium, sodium, magnesium, calcium and barium). Suitable peroxy compounds include hydrogen peroxide, peroxides of alkali and alkaline earth metals, organic peroxy compounds and peroxy acids and salts thereof. Any orally acceptable compound that delivers a perhydroxy (OOH<->) ion is useful. A peroxy compound can optionally be present in a form of a polymer-peroxide complex, for example a polyvinylpyrrolidone-hydrogen peroxide complex.

Peroxides of alkali and alkaline earth metals include lithium peroxide, potassium peroxide, sodium peroxide, magnesium peroxide, calcium peroxide and barium peroxide.

Organic peroxy compounds include, for example, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and the like.

Peroxy acids and their salts include organic peroxy acids such as alkyl peroxy acids and monoperoxyphthalate, as well as inorganic peroxy acid salts including persulfate, dipersulfate, percarbonate, perphosphate, perborate and persilicate salts of alkali and alkaline earth metals such as lithium, potassium, sodium, magnesium, calcium and barium. Another useful peroxy compound is sodium pyrophosphate peroxyhydrate.

One aspect of this embodiment is that the first acid is an acid selected from the group consisting of acetic acid ($pK_a$=4.76), ascorbic acid ($pK_a$=4.10), benzoic acid ($pK_a$=4.2), citric acid ($pK_a$=4.74), p-methoxybenzoic acid ($pK_a$=4.47) and propionic acid ($pK_a$=4.87) and the second acid is selected from the group consisting of chloric acid, hydrochloric acid, nitric acid, phosphoric acid, sulfuric acid, and sulfurous acid. In another aspect of this embodiment, the first acid is citric acid and the second acid is phosphoric acid.

In another aspect of this embodiment is that the second acid has a first $pK_a$ of between 1.5-2.5 and a second $pK_a$ of between 6.5-7.5, e.g. phosphoric acid ($pK_{a1}'$=2.1; $pK_{a2}$=7.2) or sulfurous acid ($pK_{a1}$=1.8; $pK_{a2}$=6.9).

In one embodiment, the invention provides a mouthwash comprising hydrogen peroxide in an amount effective to whiten the teeth, together with a combination of citric acid and phosphoric acid in an amount sufficient to provide a pH of 3-6, with one embodiment being a pH of 4 to 5.5. For example, the invention provides 1.1. Mouthwash 1 wherein the hydrogen peroxide is present in an amount of from 0.01-5%, e.g., in an amount of 1-3%, e.g., about 2%.
1.2. Any of the foregoing mouthwashes wherein the phosphoric acid and citric acid are present in a ratio of 1:1 to 10:1.
1.3. Any of the foregoing mouthwashes wherein the amount of phosphoric acid is from 0.01-1.5%, e.g., 0.5-1%, e.g., about 0.7%.
1.4. Any of the foregoing mouthwashes, wherein the amount of citric acid is from 0.01-0.5%, e.g., 0.1-0.3%, e.g., about 2%.
1.5. Any of the foregoing mouthwashes further comprising an acidic polymer, e.g., a polymer selected from polycarboxylate polymers and polyvinyl methyl ether/maleic anhydride (PVME/MA) copolymers.
1.6. Any of the foregoing mouthwashes further comprising an anticalculus-effective amount of one or more pyrophosphate salts, e.g., selected from dialkali or tetraalkali metal pyrophosphate salts, e.g. $Na_4P_2O_7$ (tetrasodium pyrophosphate or TSPP), $K_4P_2O_7$ (tetrapotassium pyrophosphate or TKPP), $Na_2K_2P_2O_7$, $Na_2H_2P_2O_7$ and $K_2H_2P_2O_7$ and combinations thereof, for example, in a total amount of 0.5-5%, e.g., 1-3%.

1.7. Any of the foregoing mouthwashes comprising a combination of TSPP and TKPP, e.g., in a total amount of 1-3%, e.g., in a ratio of from 1:1 to 1:5, for example comprising in one embodiment about 0.3-0.6%, e.g., 0.4-0.5% of TSPP and 1.2-1.5%, e.g. 1.3-1.4% of TKPP.

1.8. Any of the foregoing mouthwashes comprising one or more humectants, e.g., selected from glycerin, propylene glycol, sorbitol, and combinations of two or more thereof, e.g., in a total amount of 1-40%.

1.9. Any of the foregoing mouthwashes comprising a non-saccharide sweetener and/or a saccharide sweetener, e.g., a sweetening amount of a combination of saccharin and sucralose, e.g., in a ratio selected from the group consisting of 1:1-20:1 and 10:1-15:1, e.g., about 0.025% sodium saccharin and about 0.002% sucralose.

1.10. Any of the foregoing mouthwashes comprising one or more flavorings or coolants, e.g., comprising a combination of menthol and methyl salicylate, e.g., in a ratio of about 0.5:1 to 1.5:1, e.g. in a total amount of 0.1-1%.

1.11. Any of the foregoing mouthwashes comprising one or more surfactants, e.g., one or more nonionic surfactants, e.g, comprising one or more poloxamers and/or polysorbates, e.g. polysorbate 20.

1.12. Any of the foregoing mouthwashes comprising an antimicrobially effective amount of an antibacterial agent, e.g., selected from triclosan and cetylpyridinium chloride.

1.13. Any of the foregoing mouthwashes comprising an effective amount of fluoride.

1.14. Any of the foregoing mouthwashes comprising an effective amount of a basic amino acid, e.g., arginine, in free or orally acceptable salt form.

1.15. Any of the foregoing mouthwashes which is an aqueous solution.

1.16. Any of the foregoing mouthwashes comprising one or more or all of the following ingredients in the following amounts:

| | |
|---|---|
| Water | 60-80% |
| Polyphosphate salt | 1.1-3%, e.g. about 1.8% |
| Non-saccharide sweetener | 0.01-0.05%, e.g., about 0.025% |
| Saccharide sweetener | 0.001-0.005%, e.g., about 0.002% |
| Organic acid | 0.6-2.0%, e.g., about 0.9% |
| Polyhydric alcohol (humectant) | 7-45%, e.g., about 20% |
| Surfactant | 0.5-2%, e.g., about 1% |
| Whitening agent | 0.5-5%, e.g. about 2% |
| Flavorant | 0.2-2%, e.g., about 0.22% |

One embodiment of the mouthwash comprises:

| | |
|---|---|
| Water | 60-80%, e.g., about 70% |
| TSPP | 0.1-1%, e.g., about 0.45% |
| TKPP | 1-2%, e.g., about 1.35% |
| Sodium saccharin | 0.01-0.05%, e.g., about 0.025% |
| Sucralose | 0.001-0.005, e.g., about 0.002% |
| Phosphoric acid | 0.5-1.5%, e.g., about 0.7% |
| Citric acid | 0.1-0.5%, e.g., about 0.2% |
| Humectant | 0.1-0.5%, e.g., about 0.2% |
| Surfactant | 0.1-0.5%, e.g., about 0.2% |
| Hydroxide peroxide | 0.5-5%, e.g. about 2% |
| Flavor | 0.02-2%, e.g., about 0.22% |
| PYME/MA (e.g. Gantrez ®) | 1-2%, e.g., about 1.5% |

Some embodiments of the present invention provide a method of whitening teeth comprising administering any of the mouthwashes described herein, e.g., Mouthwash 1, et seq., to the oral cavity of subject in need thereof. In some embodiments, the administering comprises rinsing for from about 15 to about 60 seconds. In some embodiments, the administering comprises rinsing for from about 30 seconds. The invention further provides mouthwashes as described herein, e.g., Mouthwash 1, et seq., for use in a method of whitening teeth.

The invention further provides the use of a combination of phosphoric acid and citric acid in the manufacture of a mouthwash comprising hydrogen peroxide, e.g., in the manufacture of any of the mouthwashes described herein, e.g., Mouthwash 1, et seq.

In some embodiments, there is a fluoride source is present in an amount effective to provide from about 90 to about 500 ppm of fluoride. In other embodiments, the fluoride source is present in an amount effective to provide about 225 ppm of fluoride. In some embodiments, the fluoride source is selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination of two or more thereof. In some embodiments, the fluoride source is selected from sodium fluoride; sodium monofluorophosphate; and a combination thereof. In other embodiments, the fluoride source comprises sodium fluoride. In some embodiments, the fluoride source is present in an amount from about 0.02% to about 0.2%, by weight, of the composition. In some embodiments, the fluoride source is present in an amount from about 0.03% to about 0.08%, by weight, of the composition. Other embodiments provide a composition wherein the fluoride source is present in the amount of about 0.05%, by weight, of the composition. In some embodiments, the fluoride source is present in the amount of 0.5%, by weight, of the composition.

In some embodiments, there is a basic amino acid, e.g., comprising L-arginine in free or orally acceptable salt form. In some embodiments, the basic amino acid is selected from arginine free base, arginine hydrochloride, arginine phosphate, arginine bicarbonate, and combinations thereof. In some embodiments, the effective amount of the basic amino acid in free or orally acceptable salt form comprises 0.05 to 2% by weight of the formulation (measured as the weight of the free base equivalent when in orally acceptable salt form).

Some embodiments further comprise a buffering agent. In some embodiments, the buffering agent is a sodium phosphate buffer (e.g., sodium phosphate monobasic and disodium phosphate).

Other embodiments further comprise a humectant, e.g., a polyhydric alcohol selected from glycerin, sorbitol, propylene glycol, and a combination of two or more thereof. Humectants useful herein include polyhydric alcohols such as glycerin, sorbitol, xylitol or low molecular weight PEGs, alkylene glycol such as polyethylene glycol or propylene glycol. In various embodiments, humectants are operable to prevent hardening of paste or gel compositions upon exposure to air. In various embodiments humectants also function as sweeteners. In some embodiments, the humectant is present in the amount of about 1 to about 40% each by weight. In some embodiments, the humectant is sorbitol. In some embodiments sorbitol present at a concentration of from about 5 to about 25%, by weight. In some embodiments sorbitol present at a concentration of from about 5 to about 15%, by weight. In some embodiments, the sorbitol is present at a concentration of about 7-10%, by weight. Reference to sorbitol herein are adjusted to refer to the material by dry weight, although the material is typically as available commercially in 70% aqueous solutions. In some embodiments, the total humectant concentration is from about 1 to about 60%, by weight. In some embodiments, the humectant is glycerin. In some embodiments, glycerin is present at a concentration of from about 5 to about 15%, by weight. In some embodiments, glycerin present is at a concentration of about 7.5%, by weight. In some embodiments, the humectant is propylene glycol. In some embodiments, propylene glycol is present at a concentration of about 5 to about 15%, by weight. In some embodiments, propylene glycol is present at a concentration of about 7%, by weight.

Still other embodiments further comprise an antibacterial agent, e.g., triclosan or cetylpyridinium chloride. Antibacterially effective amounts of such agents in a mouthwash formulation are about 0.01-0.1%, e.g., about 0.03% for triclosan or about 0.07% for cetyl pyridinium chloride.

Acidic polymers, for example polyacrylate gels, may be provided in the form of their free acids or partially or fully neutralized water soluble alkali metal (e.g., potassium and sodium) or ammonium salts. Certain embodiments include about 1:4 to about 4:1 copolymers of maleic anhydride or acid with another polymerizable ethylenically unsaturated monomer, for example, methyl vinyl ether(methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation. Other operative polymers include those such as the 1:1 copolymers of maleic anhydride with ethyl acrylate, hydroxyethyl methacrylate, N-vinyl-2-pyrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers may contain sufficient carboxylic salt groups for water-solubility. The acidic polymers or copolymers may be present at levels of from 0.1-5%, e.g., 1-2% for PVME/MA.

The compositions of the invention are intended for topical use in the mouth and so any salts for use in the present invention should be orally acceptable, that is, safe for topical use in the mouth, in the amounts and concentrations provided. Suitable salts include salts known in the art to be pharmaceutically acceptable salts, which are generally considered to be orally acceptable for this purpose in the amounts and concentrations provided. Orally acceptable salts include those derived from pharmaceutically acceptable inorganic or organic acids or bases, for example acid addition salts formed by acids which form a physiological acceptable anion, e.g., hydrochloride salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In some embodiments the compositions further comprise one or more components selected from a fluoride ion source; a tartar control agent; a buffering agent; an abrasive; and a combination of two or more thereof. In some embodiments, at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Although the peroxide is generally effective control microbes, in some embodiments an additional preservative is present. In some embodiments, the preservative is selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of from about 0.0001 to about 1%, by weight. In some embodiments, the preservative is present at a concentration of from about 0.01 to about 1%, by weight. In some embodiments, the preservative is present at a concentration of about 0.5%, by weight.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-δ-3,5-cycl-ohexadienimine], FD&C Blue No. 1 (disodium salt of dibenzyldiethyl-diamino-triphenylcarbinol trisulfonic acid anhydride), FD&C Blue No. 2 (sodium salt of disulfonic acid of indigotin) and mixtures thereof in various proportions. Typically, colorants if included are present in very small quantities.

Flavor agents are known, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Typically, flavorants if included are present at 0.01-1%, by weight. In some embodiments, flavoring may be present in about 0.2%, by weight.

Sweeteners include both natural and artificial sweeteners. Suitable sweetener include, but are not limited to water soluble saccharide sweetening agents such as monosaccharides, disaccharides and polysaccharides such as xylose, ribose, glucose (dextrose), mannose, galactose, fructose (levulose), sucrose (sugar), maltose, and water soluble artificial non-saccharide sweeteners such as the soluble saccharin salts, i.e., sodium or calcium saccharin salts, cyclamate salts dipeptide based sweeteners, such a L-aspartic acid derived sweeteners, such as L-aspartyl-L-phenylalanine methyl ester (aspartame). In general, the effective amount of sweetener is utilized to provide the level of sweetness desired for a particular composition, will vary with the sweetener selected. This amount will normally be about 0.001% to about 5% by weight of the composition. In some embodiments, the sweetener is a combination of sucralose present at 0.001-0.003% and sodium saccharin present at about 0.01-0.03% by weight of the composition.

Optional breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium.

In a particular embodiment, the mouthwash comprises pyrophosphate salts having anticalculus efficacy useful in the practice of the present invention include water soluble salts such as dialkali or tetraalkali metal pyrophosphate salts such as $Na_4P_2O_7$ (TSPP), $K_4P_2O_7$ (TKPP), $Na_2K_2P_2O_7$, $Na_2H_2P_2O_7$ and $K_2H_2P_2O_7$. Polyphosphate salts include the water soluble alkali metal tripolyphosphates such as sodium tripolyphosphate and potassium tripolyphosphate. The pyrophosphate salts are incorporated in the dentifrice composition of the present invention at a concentration of about 0.5 to about 2% by weight, and preferably about 1.5 to about 2% by weight and the polyphosphate salts are incorporated in the dentifrice composition of the present invention at a concentration of about 1 to about 7% by weight. In some embodiments, tartar control agent is present at a concentration of from about 0.01 to 10%, by weight. In some embodiments, the tartar control agent is present at a concentration of about 1%, by weight. In some embodiments, the tartar control agent also acts as a buffer. For example, in a phosphate buffer system, sodium phosphate monobasic is present at a concentration of from about 0.01 to about 5%, by weight and disodium phosphate is present at a concentration of from about 0.01 to about 5%, by weight, the precise ratio depending upon the other excipients in the formulation and the desired pH.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, saliva stimulating agent, useful for example in amelioration of dry mouth may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof. In some embodiments, a local or systemic analgesic such as aspirin, codeine, acetaminophen, sodium salicylate or triethanolamine salicylate can be used.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Mouthwash Formulations

Mouthwash formulations comprising various combinations of acids with hydrogen peroxide are described in Table 1 (below).

TABLE 1

|  | Composition 1 | Composition 2 | Composition 3 | Composition 4 |
|---|---|---|---|---|
| Water | 73.95 | 73.95 | 73.95 | 73.95 |
| TSPP | 0.45 | 0.45 | 0.45 | 0.45 |
| TKPP | 1.35 | 1.35 | 1.35 | 1.35 |
| Sodium saccharin | 0.025 | 0.025 | 0.025 | 0.025 |
| Sucralose | 0 | 0 | 0 | 0.002 |
| Phosphoric acid | 1.00 | 0 | 0.80 | 0.80 |
| Citric acid | 0 | 1.00 | 0.20 | 0.20 |

TABLE 1-continued

|  | Composition 1 | Composition 2 | Composition 3 | Composition 4 |
|---|---|---|---|---|
| Humectant | 20 | 20 | 20 | 20 |
| Surfactant | 1.00 | 1.00 | 1.00 | 1.00 |
| Hydrogen peroxide | 2.00 | 2.00 | 2.00 | 2.00 |
| Flavor | 0.22 | 0.22 | 0.22 | 0.22 |

Example 2

Expert Sensory Assessment

The formulations of Compositions 1-4 were evaluated by sensory experts, with sourness and bitter aftertaste each evaluated on a scale of 1-5, with one being not at all sour/bitter and 5 being extremely sour/bitter. A score of 4 or 5 for either parameter or 3's on both parameters is considered unacceptable.

TABLE 2

| 1 | 2% $H_2O_2$/TSPP/TKPP/Phosphoric acid/ Saccharin | Sour (3)/bitter aftertaste (3) |
| 2 | 2% $H_2O_2$/TSPP/TKPP/Citric acid/ Saccharin | Sour (4)/bitter aftertaste (3) |
| 3 | 2% $H_2O_2$/TSPP/TKPP/Citric acid/Phosphoric/Saccharin | Sour (2)/bitter aftertaste (3) |
| 4 | 2% $H_2O_2$/TSPP/TKPP/Phosphoric/ Citric acid/Saccharin/Sucralose | Sour (2)/bitter aftertaste (2) |

Based on this study, Compositions 1 and 2 were found unacceptable. Composition 4 is preferred, as being less sour and having a less bitter aftertaste.

Example 3

Consumer Testing

Composition 4 is further modified with the addition of 1.5% Gantrez®, a co-polymer of polymethylvinyl ether and maleic anhydride, and the formulations with and without Gantrez® were tested in a consumer test protocol. A total of 120 regular mouthwash users participated in the monadic home use test for the mouthwash. Each participant was instructed to use the product for 5 days. At the end of the usage period, the participants were asked to rate the overall liking of the mouthwash using a scale of 1-9, with 1 being "dislike extremely" and 9 being "like extremely". The total percentage of participants who gave the overall liking score of 7-9 was reported. The test formula and results are listed in Table 3 below.

TABLE 3

|  | Composition 4 | Composition 5 |
|---|---|---|
| Water | 73.95 | 72.45 |
| TSPP | 0.45 | 0.45 |
| TKPP | 1.35 | 1.35 |
| Gantrez ® | 0 | 1.51 |
| Sodium saccharin | 0.025 | 0.025 |
| Sucralose | 0.002 | 0.002 |
| Phosphoric acid | 0.8 | 0.8 |
| Citric Acid | 0.2 | 0.2 |
| Humectant | 20 | 20 |
| Surfactant | 1 | 1 |
| Hydrogen peroxide | 2 | 2 |
| Flavor | 0.22 | 0.22 |
| Consumer test results (Overall liking) | 23.8% | 29.5% |

Composition 5 was found to be more palatable and preferred by consumers and displayed a 24% increase in overall liking (29.5−23.8)/(23.8)×100%).

Having thus described in detail various embodiments of the present invention, it is to be understood that the invention defined by the above paragraphs is not to be limited to particular details set forth in the above description as many apparent variations thereof are possible without departing from the spirit or scope of the present invention.

the invention claimed is:

1. A mouthwash comprising a whitening agent in an amount effective to whiten the teeth, wherein the whitening agent is hydrogen peroxide, optionally together with one or more additional whitening agents, and a combination of a first acid and a second acid, wherein the first acid comprises citric acid and the second acid comprises phosphoric acid, wherein the citric acid and phosphoric acid are in an amount sufficient to provide a pH of 3 to 6, and wherein the mouthwash comprises water in an amount of 60% to 80%.

2. The mouthwash according to claim 1 wherein the hydrogen peroxide is present in an amount of from 0.01-5%.

3. The mouthwash according to claim 2 wherein citric acid and phosphoric acid are present in a ratio of 1:1 to 1:10.

4. The mouthwash according to claim 3 wherein the amount phosphoric acid is from 0.01-1.5%.

5. The mouthwash according claim 4 wherein the amount of citric acid is from 0.01-0.5%.

6. The mouthwash according to claim 5 further comprising a polymer selected from polycarboxylate polymers and polyvinyl methyl ether/maleic anhydride (PVME/MA) copolymers.

7. The mouthwash according to claim 1 further comprising an anticalculus-effective amount of one or more pyrophosphate salts selected from dialkali or tetraalkali metal pyrophosphate salts.

8. The mouthwash according to claim 1 further comprising sweetening amount of a combination of saccharin and sucralose.

9. The mouthwash according to claim 1 further comprising a combination of menthol and methyl salicylate.

10. The mouthwash according to claim 1 further comprising an anti-microbially effective amount of an antibacterial agent selected from triclosan and cetylpyridinium chloride.

11. The mouthwash according to claim 1 comprising one or more or all of the following ingredients in the following amounts:

| Polyphosphate salt | 1.1-3%, |
| Non-saccharide sweetener | 0.01-0.05%, |

-continued

| | |
|---|---|
| Saccharide sweetener | 0.001-0.005%, |
| Polyhydric alcohol (humectant) | 7-45%, |
| Surfactant | 0.5-2%, |
| Flavorant | 0.2-2%. |

12. The mouthwash according to claim 11, which comprises:

| | |
|---|---|
| Water | 60-80%, |
| TSPP | 0.1-1%, |
| TKPP | 1-2%, |
| Sodium saccharin | 0.01-0.05%, |
| Sucralose | 0.001-0.005, |
| Phosphoric acid | 0.5-1.5%, |
| Citric acid | 0.1-0.5%, |
| Humectant | 0.1-0.5%, |
| Surfactant | 0.1-0.5%, |
| Hydroxide peroxide | 0.5-5%, |
| Flavor | 0.02-2%, |
| PYME/MA (e.g. Gantrez ®) | 1-2%. |

13. A method of whitening teeth comprising administering a mouthwash according to claim 1 to the oral cavity of subject in need thereof.

* * * * *